(12) United States Patent
Ghosh et al.

(10) Patent No.: US 7,660,675 B2
(45) Date of Patent: Feb. 9, 2010

(54) METHOD AND SYSTEM FOR ANALYSIS OF ARRAY-BASED, COMPARATIVE-HYBRIDIZATION DATA

(75) Inventors: Jayati Ghosh, Sunnyvale, CA (US); Amir Ben-dor, Bellevue, WA (US); Anya Tsalenko, Chicago, IL (US); Bo Curry, Redwood City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 521 days.

(21) Appl. No.: 11/492,472

(22) Filed: Jul. 24, 2006

(65) Prior Publication Data

US 2008/0120038 A1 May 22, 2008

(51) Int. Cl.
*G06F 19/00* (2006.01)
*C12Q 1/68* (2006.01)

(52) U.S. Cl. .............................. 702/19; 435/6
(58) Field of Classification Search ........................ None
See application file for complete search history.

(56) References Cited

U.S. PATENT DOCUMENTS

2006/0084067 A1   4/2006   Yakhini et al.

FOREIGN PATENT DOCUMENTS

GB         2413130      10/2005

OTHER PUBLICATIONS

Bilke et al. Detection of low level genomic alterations by comparative genomic hybridization based on cDNA micro-arrays Bioinformatics vol. 21, pp. 1138-1145 (2005).*

Lipson, D. et al., "Interval Scores for Quality Annotated CGH Data", Proceedings of the Genomic Signal Processing and Statistics Workshop, Gensips 2005, XP007906019 Newport. Rhode Island. Retrieved from the Internet: URL: http://users.isr.ist.utl.pt/Ijmrs/research/Genomics/gensips2005/papers/Gensips2005_SPSApproach140.p.df. [retrieved on Oct. 20, 2008].

Lipson, D. et al., "Efficient Calculation of Interval Scores for DNA Copy Number Data Analysis", J. Computational Biology, Mar. 2006, pp. 215-228, vol. 13, No. 2.

"Agilent CGH Analytics 3.2 Online Help" Internet Citation, 2005, pp. 85-91. XP002483250 Retrieved from the Internet: URL:http://www.chem.agilent.com/temp.rad82250/00001095.pdf. Retrieved on Jun. 5, 2008.

EP Search Report, Application No. EP 07 25 2929, dated Jun. 11, 2008.

"Agilent Oligonucleotide Array-Based CGH for Genomic DNA Analysis" Protocol Version 4.0 Jun. 2006 Agilent Technologies.

* cited by examiner

*Primary Examiner*—John S Brusca

(57) ABSTRACT

Embodiments of the present invention include methods and systems for analysis of comparative genomic hybridization ("CGH") data, including CGH data obtained from microarray experiments.

15 Claims, 14 Drawing Sheets

(3 of 14 Drawing Sheet(s) Filed in Color)

```
                        SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 1
actatgacgc tttccatcgg gctagctctc a                              31

<210> SEQ ID NO 2
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 2
tgagagctag cccgatggaa agcgtcatag t                              31

<210> SEQ ID NO 3
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 3
acuaugacgc uuuccaucgg g                                         21

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Tyr Asp Ala Phe His Arg
 1               5
```

METHOD AND SYSTEM FOR ANALYSIS OF ARRAY-BASED, COMPARATIVE-HYBRIDIZATION DATA

SUMMARY OF THE INVENTION

Embodiments of the present invention include methods and systems for analysis of comparative hybridization data, including comparative genomic hybridization ("CGH") data, such as CGH data obtained from microarray experiments. Various embodiments of the present invention include global noise based scoring methods for CGH data and methods for identifying sets of one or more contiguous chromosomal DNA subsequences that are amplified or deleted in cells from particular tissue samples. When combined with microarray-based experimental systems, method embodiments of the present invention provide markedly increased quantitative precision in the identification of chromosomal abnormalities, including amplified and deleted DNA subsequences based on CGH data. Additional embodiments of the present invention are directed to detecting, by comparative hybridization, deletion, amplifications, and other changes to general biopolymer sequences, including biopolymers other than DNA.

BRIEF DESCRIPTION OF THE DRAWINGS

The patent or application file contains at least one drawing executed in color. Copies of this patent application publication with color drawing(s) will be provided by the U.S. Patent and Trademark Office upon request and payment of the necessary fee.

DETAILED DESCRIPTION OF THE INVENTION

Embodiments of the present invention provide methods and systems for analysis of comparative genomic hybridization ("CGH") data. The methods and systems are general, and applicable to comparative hybridization data obtained from a variety of different experimental approaches and protocols. Described embodiments, below, are particularly applicable to microarray-based CGH data, obtained from high-resolution microarrays containing oligonucleotide probes that provide relatively uniform and closely-spaced coverage of the DNA sequence or sequences representing one or more chromosomes. One application for methods of the present invention is for detecting amplified and deleted genes. Examples are discussed below. However, any subsequence of chromosomal DNA may be amplified or deleted, and CGH techniques may be applied to generally detect amplification or deletion of chromosomal DNA subsequences. Comparative hybridization methods can be used to detect amplification or deletion of subsequences of any information-containing biopolymer, and other sequence changes and abnormalities.

Figure 1:
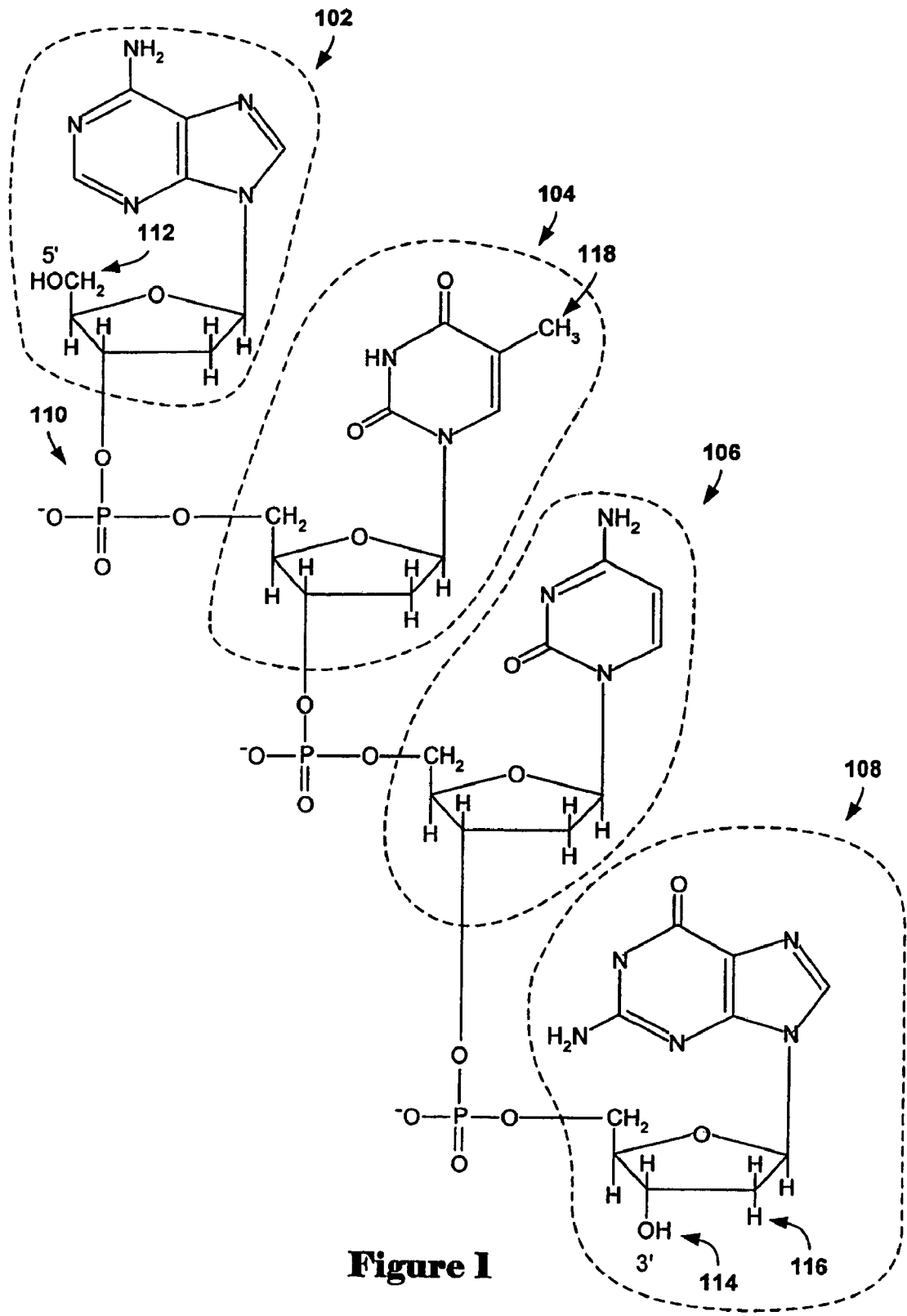
FIG. 1 shows the chemical structure of a small, four-subunit, single-chain oligonucleotide.

Prominent information-containing biopolymers include deoxyribonucleic acid ("DNA"), ribonucleic acid ("RNA"), including messenger RNA ("mRNA"), and proteins. FIG. 1 shows the chemical structure of a small, four-subunit, single-chain oligonucleotide, or short DNA polymer. The oligonucleotide shown in FIG. 1 includes four subunits: (1) deoxyadenosine 102, abbreviated "A"; (2) deoxythymidine 104, abbreviated "T"; (3) deoxycytodine 106, abbreviated "C"; and (4) deoxyguanosine 108, abbreviated "G." Each subunit 102, 104, 106, and 108 is generically referred to as a "deoxyribonucleotide," and consists of a purine, in the case of A and G, or pyrimidine, in the case of C and T, covalently linked to a deoxyribose. The deoxyribonucleotide subunits are linked together by phosphate bridges, such as phosphate 110. The oligonucleotide shown in FIG. 1, and all DNA polymers, is asymmetric, having a 5' end 112 and a 3' end 114, each end comprising a chemically active hydroxyl group. RNA is similar, in structure, to DNA, with the exception that the ribose components of the ribonucleotides in RNA have a 2' hydroxyl instead of a 2' hydrogen atom, such as 2' hydrogen atom 116 in FIG. 1, and include the ribonucleotide uridine, similar to thymidine but lacking the methyl group 118, instead of a ribonucleotide analog to deoxythymidine. The RNA subunits are abbreviated A, U, C, and G.

Figure 2:
FIG. 2 shows a symbolic representation of a short stretch of double-stranded DNA (top strand: SEQ ID NO:1; bottom strand: SEQ ID NO:2).

In cells, DNA is generally present in double-stranded form, in the familiar DNA-double-helix form. FIG. 2 shows a symbolic representation of a short stretch of double-stranded DNA. The first strand 202 is written as a sequence of deoxyribonucleotide abbreviations in the 5' to 3' direction and the complementary strand 204 is symbolically written in 3' to 5' direction. Each deoxyribonucleotide subunit in the first strand 202 is paired with a complementary deoxyribonucleotide subunit in the second strand 204. In general, a G in one strand is paired with a C in a complementary strand, and an A in one strand is paired with a T in a complementary strand. One strand can be thought of as a positive image, and the opposite, complementary strand can be thought of as a negative image, of the same information encoded in the sequence of deoxyribonucleotide subunits.

Figure 3:
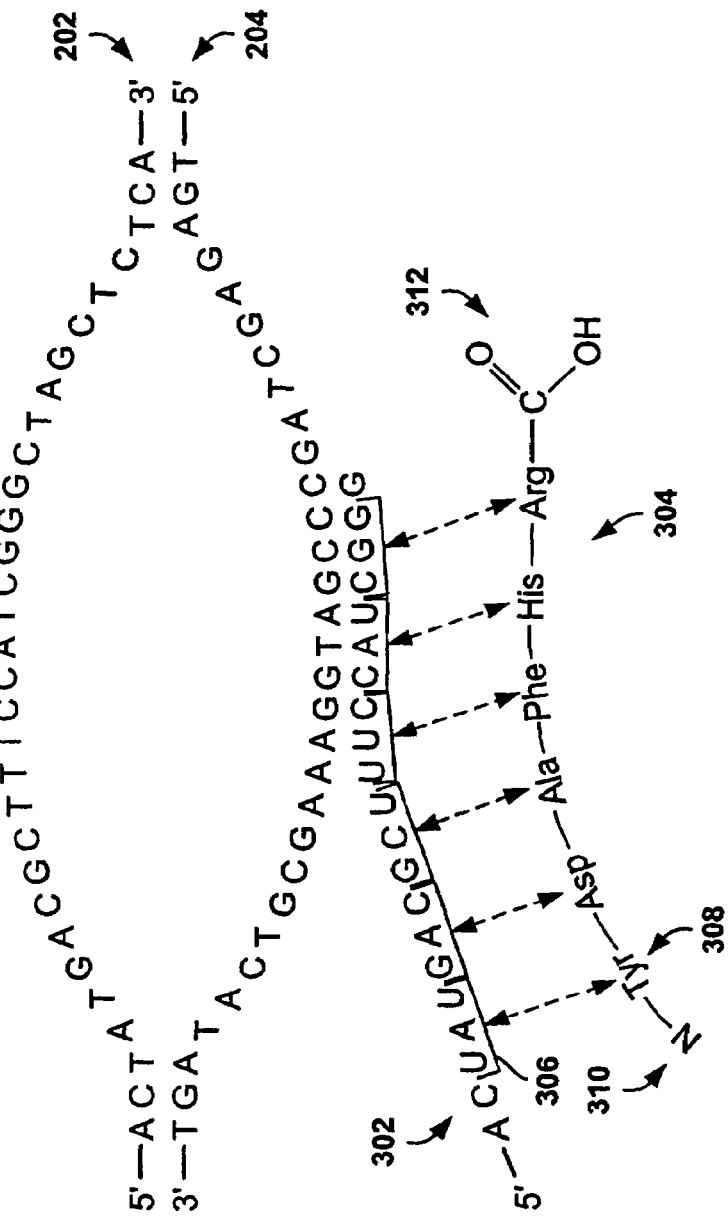
FIG. 3 illustrates construction of a protein based on the information encoded in a gene. From top to bottom :SEQ ID NO:1, SEQ ID NO:2, SEQ ID NO:3 and SEQ ID NO:4.

A gene is a subsequence of deoxyribonucleotide subunits within one strand of a double-stranded DNA polymer. A gene can be thought of as an encoding that specifies, or a template for, construction of a particular protein. FIG. 3 illustrates construction of a protein based on the information encoded in a gene. In a cell, a gene is first transcribed into single-stranded mRNA. In FIG. 3, the double-stranded DNA polymer composed of strands 202 and 204 has been locally unwound to provide access to strand 204 for transcription machinery that synthesizes a single-stranded mRNA 302 complementary to the gene-containing DNA strand. The single-stranded mRNA is subsequently translated by the cell into a protein polymer 304, with each three-ribonucleotide codon, such as codon 306, of the mRNA specifying a particular amino acid subunit of the protein polymer 304. For example, in FIG. 3, the codon "UAU" 306 specifies a tyrosine amino-acid subunit 308. Like DNA and RNA, a protein is also asymmetrical, having an N-terminal end 310 and a carboxylic acid end 312.

In eukaryotic organisms, including humans, each cell contains a number of extremely long, DNA-double-strand polymers called chromosomes. Each chromosome can be thought of, abstractly, as a very long deoxyribonucleotide sequence. Each chromosome contains hundreds to thousands of subsequences corresponding to genes. The exact correspondence between a particular subsequence identified as a gene and the protein encoded by the gene can be somewhat complicated, for reasons outside the scope of the present invention. However, for the purposes of describing embodiments of the present invention, a chromosome may be thought of as a linear DNA sequence of contiguous deoxyribonucleotide subunits that can be viewed as a linear sequence of DNA subsequences. In certain cases, the subsequences are genes, each gene specifying a particular protein. But these embodiments are far more general. Amplification and deletion of any DNA subsequence or group of DNA subsequences can be detected by the described methods, regardless of whether or not the DNA subsequences correspond to protein-sequence-specifying, biological genes, to DNA subsequences specifying various types of non-protein-encoding RNAs, or to other regions with defined biological roles. Moreover, these methods may be applied to other types of biopolymers to detect changes in biopolymer-subsequence occurrence. The term "gene" is used in the following as a notational convenience, and should be understood as simply an example of a "biopolymer subsequence." Similarly, although the described embodiments are directed to analyzing DNA chromosomal sequences, the sequences of any information-containing biopolymer are analyzable by methods of the present invention. Therefore, the term "chromosome," and related terms, are used in the following as a notational convenience, and should be understood as an example of a biopolymer or biopolymer sequence.

Figure 4:
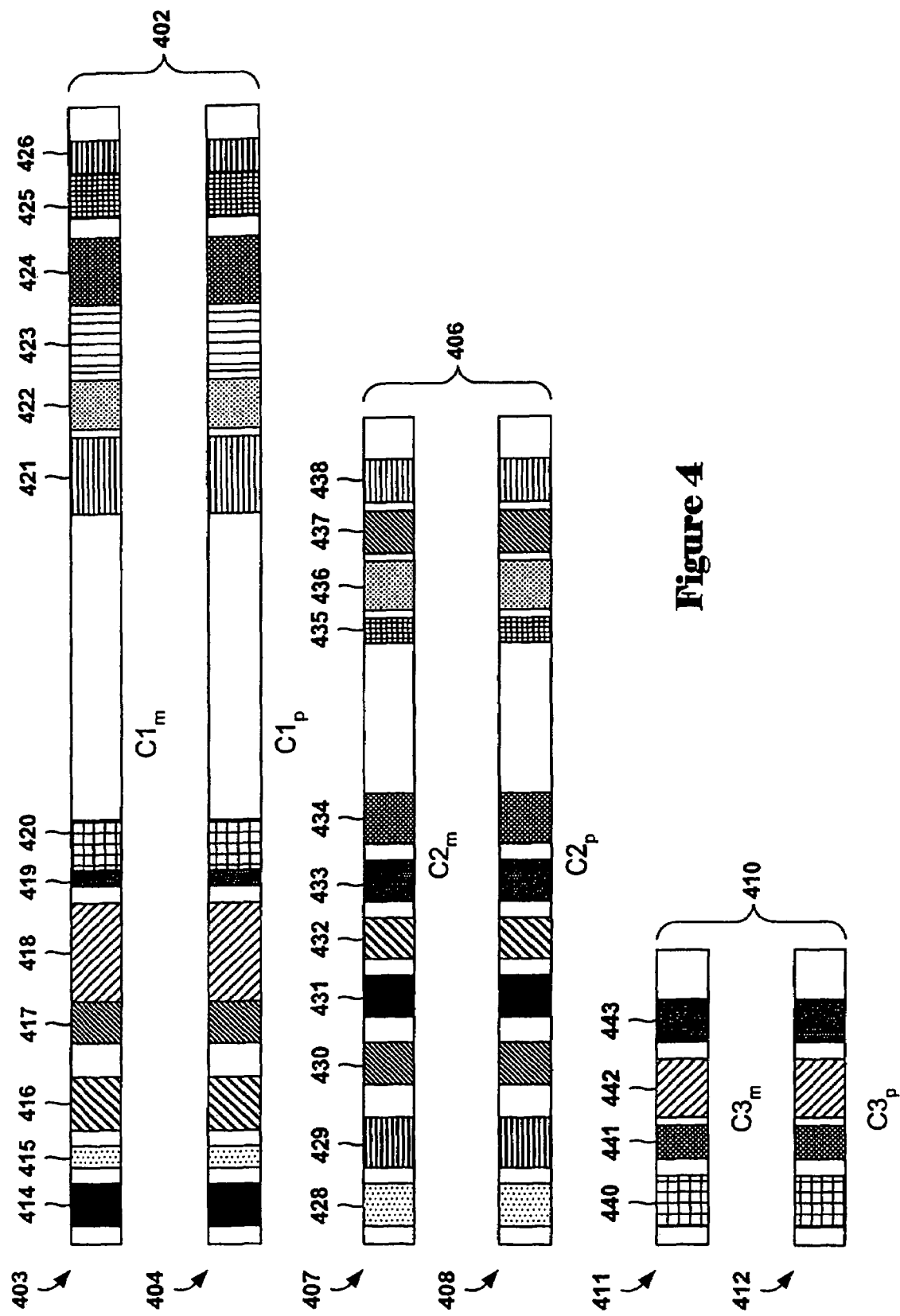
FIG. 4 shows a hypothetical set of chromosomes for a very simple, hypothetical organism.

FIG. 4 shows a hypothetical set of chromosomes for a very simple, hypothetical organism. The hypothetical organism includes three pairs of chromosomes 402, 406, and 410. Each chromosome in a pair of chromosomes is quite similar, generally having identical genes at identical positions along the lines of the chromosome. In FIG. 4, each gene is represented as a subsection of the chromosome. For example, in the first chromosome 403 of the first chromosome pair 402, 13 genes are shown, 414-426.

As shown in FIG. 4, the second chromosome 404 of the first pair of chromosomes 402 includes the same genes at the same positions. Each chromosome of the second pair of chromosomes 406 includes eleven genes 428-438, and each chromosome of the third pair of chromosomes 410 includes four genes 440-443. Of course, in a real organism, there are generally many more chromosome pairs, and each chromosome includes many more genes. However, the simplified, hypothetical genome shown in FIG. 4 is more suitable for simply describing embodiments of the present invention. Note that, in each chromosome pair, one chromosome is originally obtained from the mother of the organism, and the other chromosome is originally obtained from the father of the organism. Thus, the chromosomes of the first chromosome pair 402 are referred to as chromosome "$C1_m$" and "$C1_p$." While, in general, each chromosome of a chromosome pair has the same genes positioned at the same location along the length of the chromosome, the genes inherited from one parent may differ slightly from the genes inherited from the other parent. Different versions of a gene are referred to as alleles. Common differences include single-deoxyribonucle-otide-subunit substitutions at various positions within the DNA subsequence corresponding to a gene.

Figure 5:
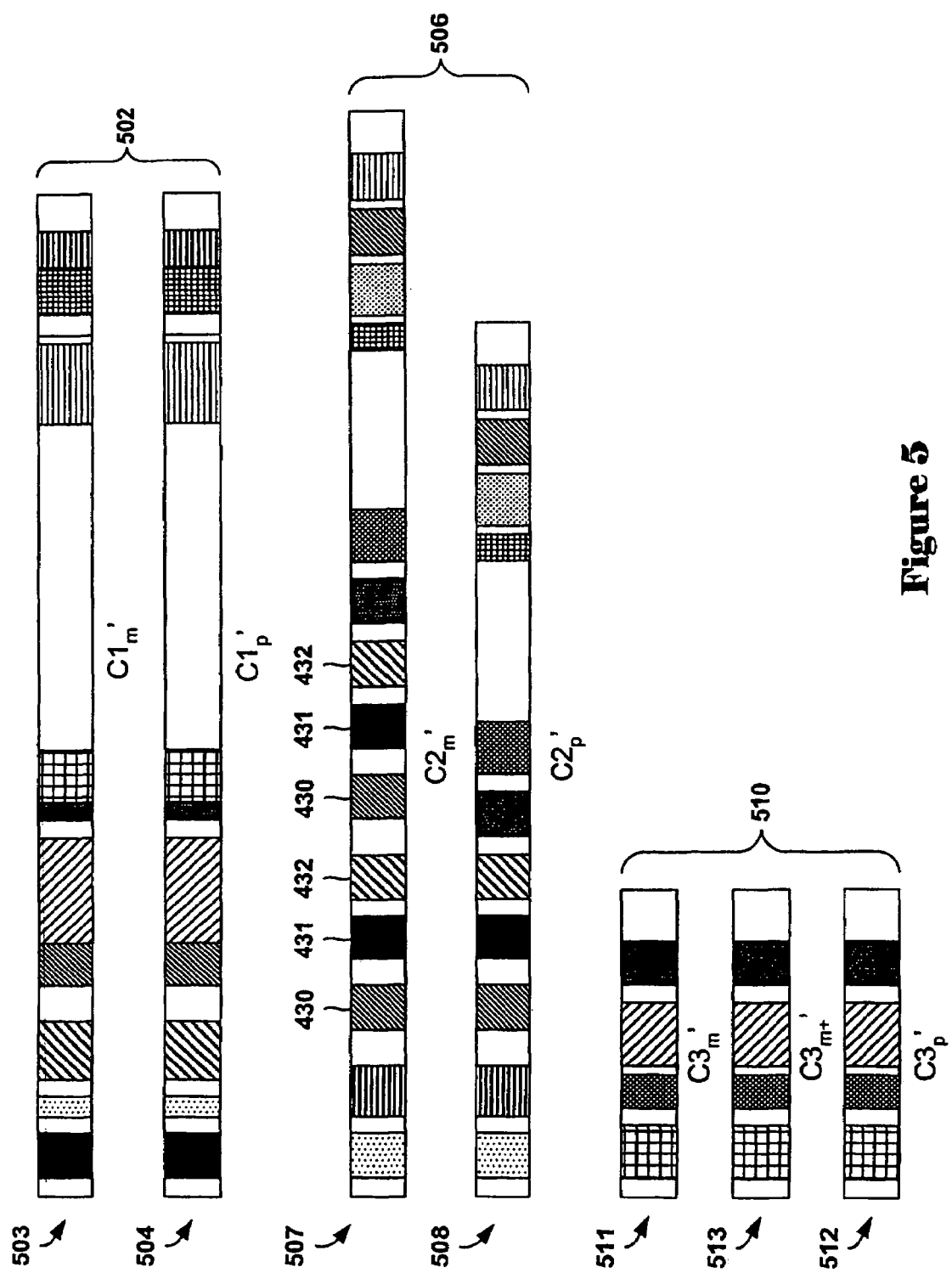
FIG. 5 shows examples of gene deletion and gene amplification in the context of the hypothetical genome shown in FIG. 4.

Although differences between genes and mutations of genes may be important in the predisposition of cells to various types of cancer, and related to cellular mechanisms responsible for cell transformation, cause-and-effect relationships between different forms of genes and pathological conditions are often difficult to elucidate and prove, and very often indirect. However, other genomic abnormalities are more easily associated with pre-cancerous and cancerous tissues. Two prominent types of genomic aberrations include gene amplification and gene deletion. FIG. 5 shows examples of gene deletion and gene amplification in the context of the hypothetical genome shown in FIG. 4. First, both chromosomes $C1_m'$ 503 and chromosome $C1_p'$ 504 of the variant, or mutant, first chromosome pair 502 are shorter than the corresponding wild-type chromosomes $C1_m$ and $C1_p$ in the first pair of chromosomes 402 shown in FIG. 4. This shortening is due to deletion of genes 422, 423, and 424, present in the wild-type chromosomes 403 and 404, but absent in the variant chromosomes 503 and 504. This is an example of a double, or homozygous-gene-deletion. Small scale variations of DNA copy numbers can also exist in normal cells. These can have phenotypic implications, and can also be measured by CGH methods and analyzed by the methods of the present invention.

Generally, deletion of multiple, contiguous genes is observed, corresponding to the deletion of a substantial subsequence from the DNA sequence of a chromosome. Much smaller subsequence deletions may also be observed, leading to mutant and often nonfunctional genes. A gene deletion may be observed in only one of the two chromosomes of a chromosome pair, in which case a gene deletion is referred to as being heterozygous. A second chromosomal abnormality in the altered genome shown in FIG. 5 is duplication of genes 430, 431, and 432 in the maternal chromosome $C2_m'$ 507 of the second chromosome pair 506. Duplication of one or more contiguous genes within a chromosome is referred to as gene amplification. In the example altered genome shown in FIG. 5, the gene amplification in chromosome $C2_m'$ is heterozygous, since gene amplification does not occur in the other chromosome of the pair $C2_p'$ 508. The gene amplification illustrated in FIG. 5 is a two-fold amplification, but three-fold and higher-fold amplifications are also observed. An extreme chromosomal abnormality is illustrated with respect to the third chromosome pair (410 in FIG. 4). In the altered genome illustrated in FIG. 5, the entire maternal chromosome 511 has been duplicated from a third chromosome 513, creating a chromosome triplet 510 rather than a chromosome pair. This three-chromosome phenomenon is referred to as a trisomy in the third chromosome-pair. The trisomy shown in FIG. 5 is an example of heterozygous gene amplification, but it is also observed that both chromosomes of a chromosome pair may be duplicated, higher-order amplification of chromosomes may be observed, and heterozygous and homozygous deletions of entire chromosomes may also occur, although organisms with such genetic deletions are generally not viable.

Figure 6:
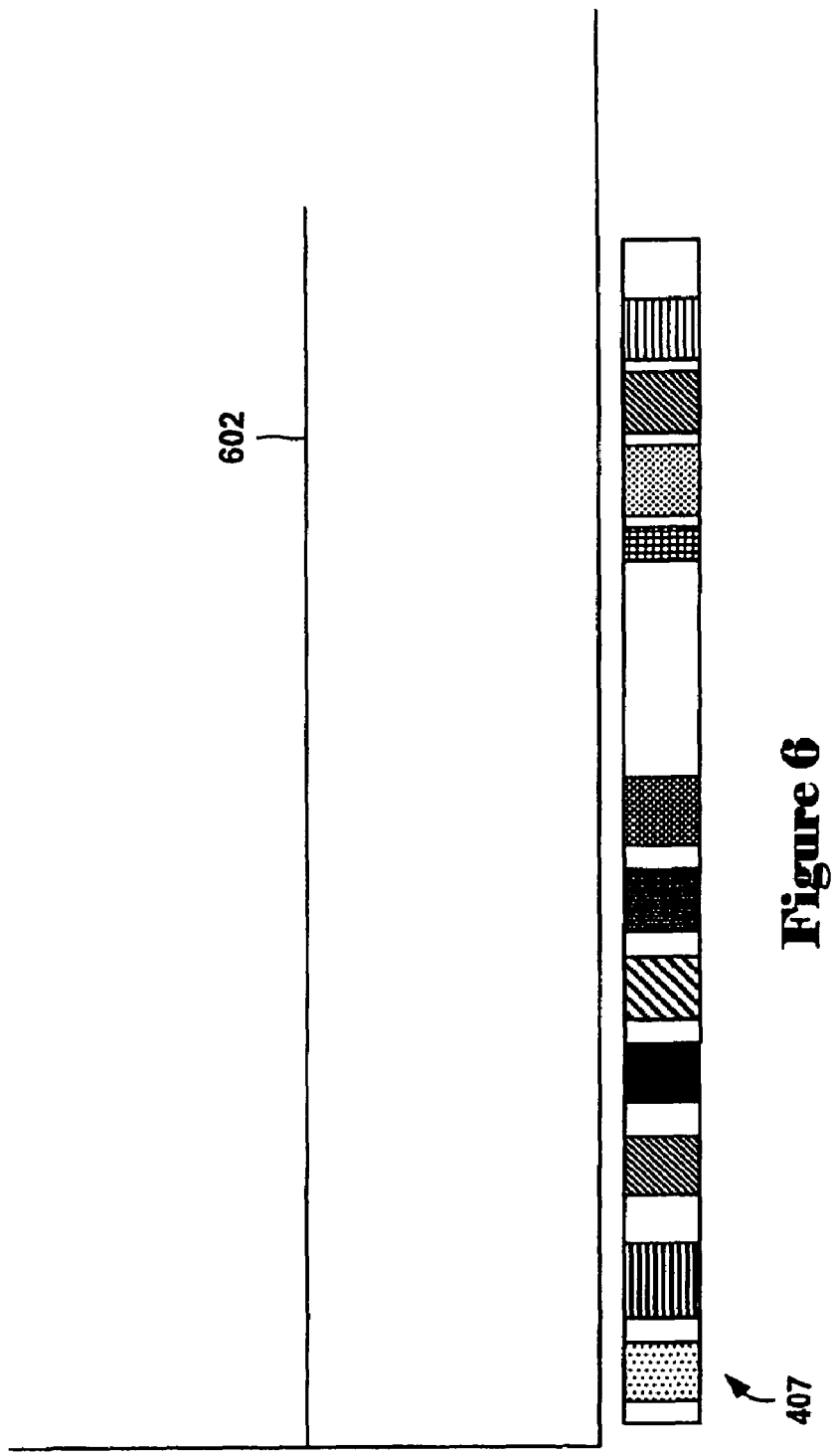
FIGS. 6-7 illustrate detection of gene amplification by CGH.
Figure 7:
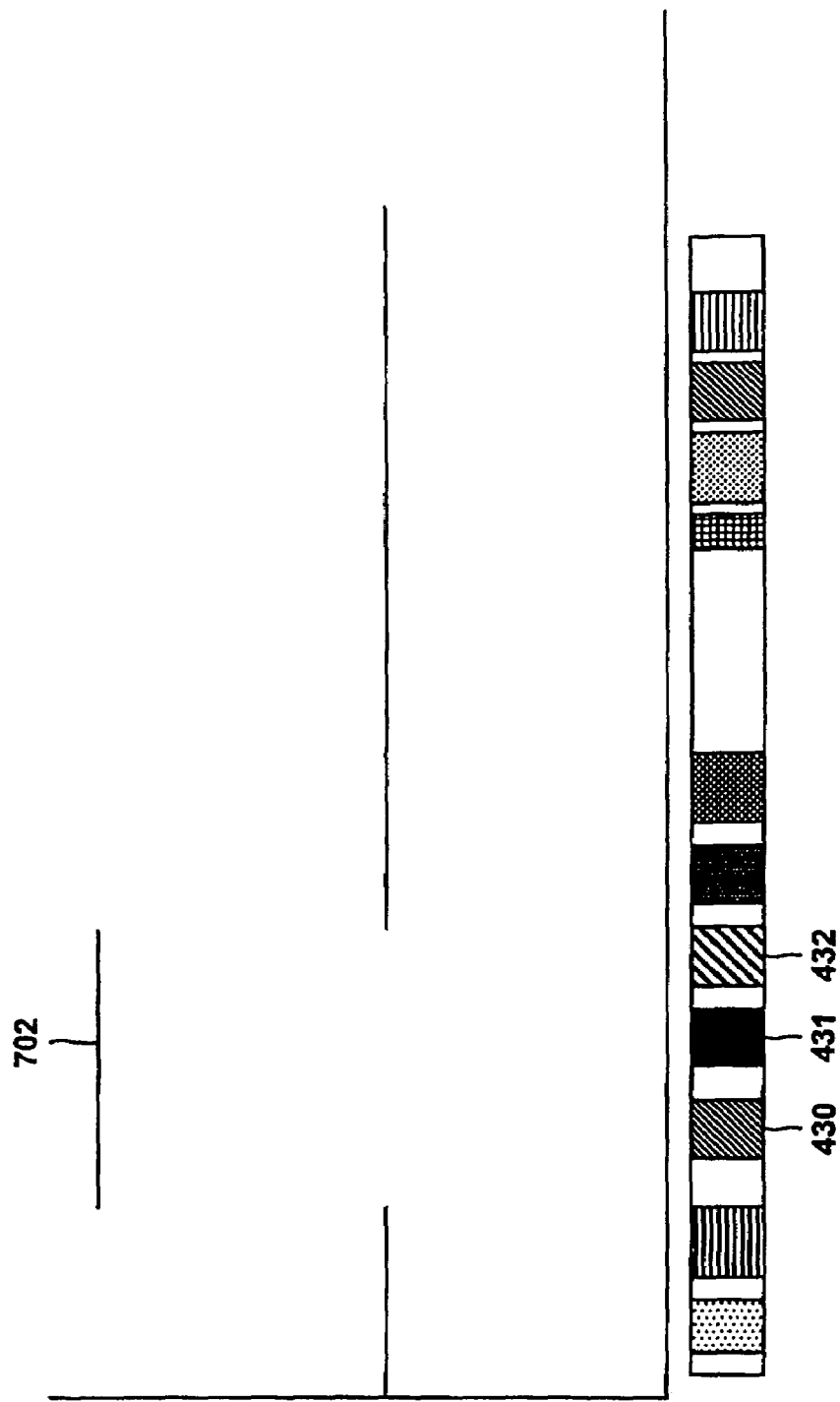
Figure 8:
FIGS. 8-9 illustrate detection of gene deletion by CGH.
Figure 9:
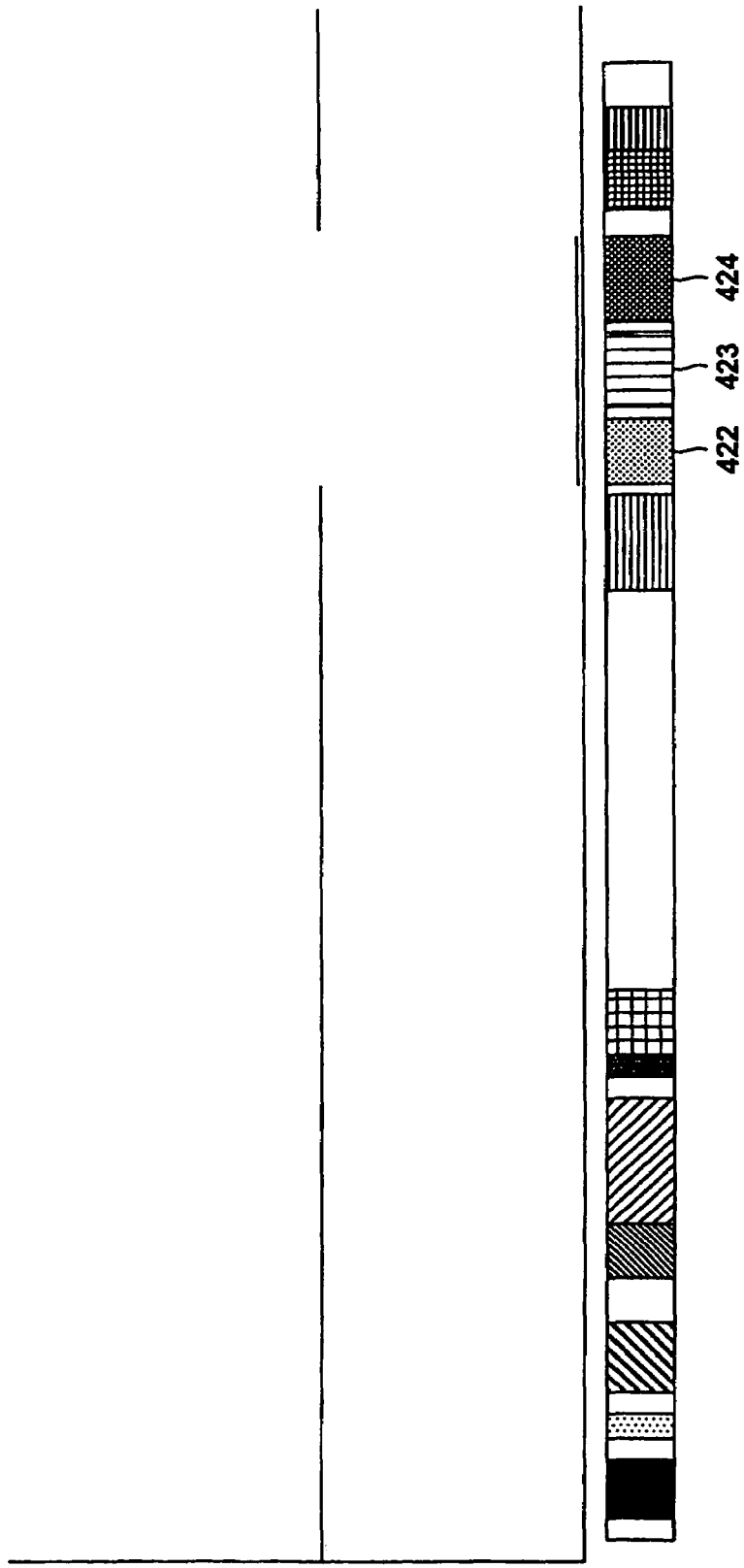

Changes in the number of gene copies, either by amplification or deletion, can be detected by comparative genomic hybridization ("CGH") techniques. FIGS. 6-7 illustrate detection of gene amplification by CGH, and FIGS. 8-9 illustrate detection of gene deletion by CGH. CGH involves analysis of the relative level of binding of chromosome fragments from sample tissues to single-stranded, normal chromosomal DNA. The tissues-sample fragments hybridize to complementary regions of the normal, single-stranded DNA by complementary binding to produce short regions of double-stranded DNA. -Hybridization occurs when a DNA fragment is exactly complementary, or nearly complementary, to a subsequence within the single-stranded chromosomal DNA. In FIG. 6, and in subsequent figures, one of the hypothetical chromosomes of the hypothetical wild-type genome shown in FIG. 4 is shown below the x axis of a graph, and the level of sample fragment binding to each portion of the chromosome is shown along with the y axis. In FIG. 6, the graph of fragment binding is a horizontal line 602 indicative of generally uniform fragment binding along the length of the chromosome 407. Of course, in an actual experiment, uniform and complete overlap of DNA fragments prepared from tissue samples may not be possible, leading to discontinuities and non-uniformities in detected levels of fragment binding along the length of a chromosome. However, in general, fragments of a normal chromosome isolated from normal tissue samples should, at least, provide a binding-level trend approaching a horizontal line, such as line 602 in FIG. 6. By contrast, CGH data for fragments prepared from the mutant genotype illustrated in FIG. 5 should generally show an increased binding level for those genes amplified in the mutant genotype.

FIG. 7 shows hypothetical CGH data for fragments prepared from tissues with the mutant genotype illustrated in FIG. 5. As shown in FIG. 7, an increased binding level 702 is observed for the three genes 430-432 that are amplified in the altered genome. In other words, the fragments prepared from the altered genome should be enriched in those gene fragments from genes which are amplified. Moreover, in quantitative CGH, the relative increase in binding should be reflective of the increase in a number of copies of particular genes.

FIG. 8 shows hypothetical CGH data for fragments prepared from normal tissue with respect to the first hypothetical chromosome 403. Again, the CGH-data trend expected for fragments prepared from normal tissue is a horizontal line indicating uniform fragment binding along the length of the chromosome. By contrast, the homozygous gene deletion in chromosomes 503 and 504 in the altered genome illustrated in FIG. 5 should be reflected in a relative decrease in binding with respect to the deleted genes. FIG. 9 illustrates hypothetical CGH data for DNA fragments prepared from the hypothetical altered genome illustrated in FIG. 5 with respect to a normal chromosome from the first pair of chromosomes (402 in FIG. 4). As seen in FIG. 9, no fragment binding is observed for the three deleted genes 422, 423, and 424.

CGH data may be obtained by a variety of different experimental techniques. In one technique, DNA fragments are prepared from tissue samples and labeled with a particular chromophore. The labeled DNA fragments are then hybridized with single-stranded chromosomal DNA from a normal cell, and the single-stranded chromosomal DNA then visually inspected via microscopy to determine the intensity of light emitted from labels associated with hybridized fragments along the length of the chromosome. Areas with relatively increased intensity reflect regions of the chromophore amplified in the corresponding tissue chromosome, and regions of decreased emitted signal indicate deleted regions in the corresponding tissue chromosome. In other techniques, normal DNA fragments labeled with a first chromophore are competitively hybridized to a normal single-stranded chromosome with fragments isolated from abnormal tissue, labeled with a second chromophore. Relative binding of normal and abnormal fragments can be detected by ratios of emitted light at the two different intensities corresponding to the two different chromophore labels.

Figure 10:
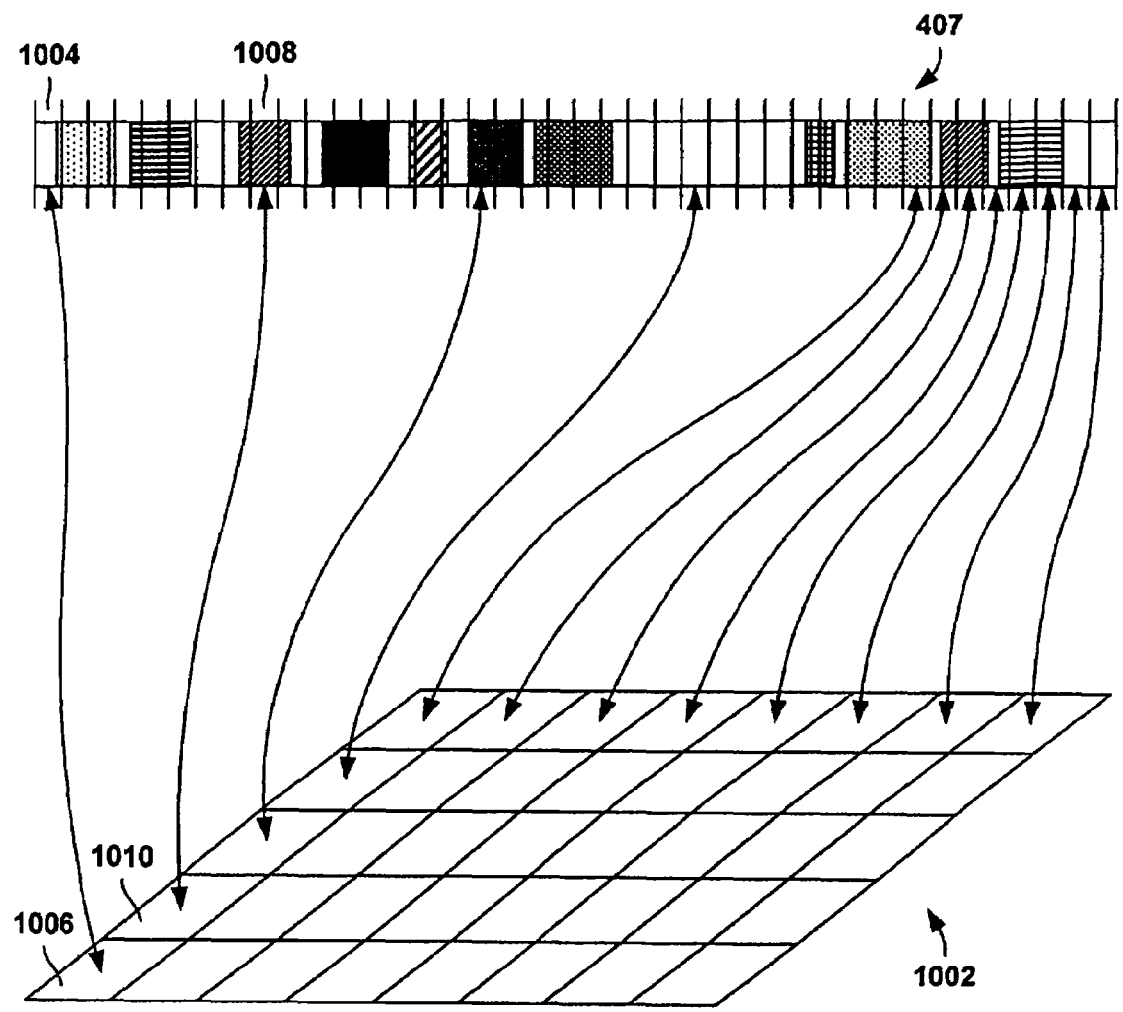
FIGS. 10-12 illustrate microarray-based CGH.
Figure 11:
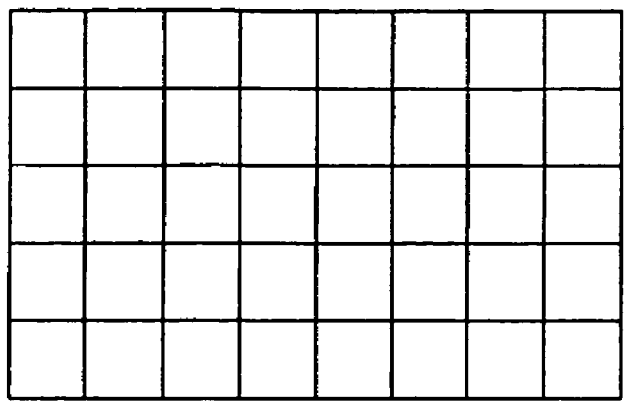
Figure 12:
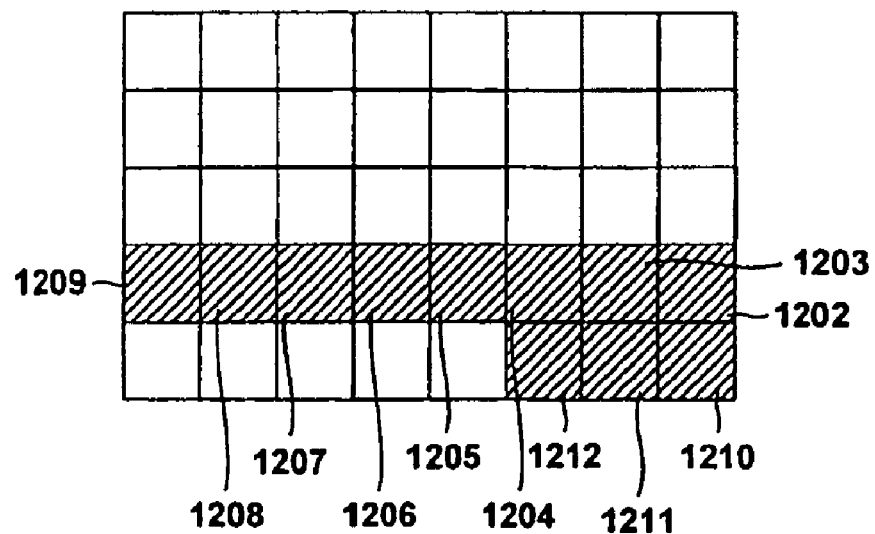

A third type of CGH is referred to as microarray-based CGH ("aCGH"). FIGS. 10-12 illustrate microarray-based CGH. In FIG. 10, synthetic probe oligonucleotides having sequences equal to contiguous subsequences of hypothetical chromosome 407 and/or 408 in the hypothetical, normal genome illustrated in FIG. 4, are prepared as features on the surface of the microarray 1002. For example, a synthetic probe oligonucleotide having the sequence of one strand of the region 1004 of chromosome 407 and/or 408 is synthesized in feature 1006 of the hypothetical microarray 1002. Similarly, an oligonucleotide probe corresponding to subsequence 1008 of chromosome 407 and/408 is synthesized to produce the oligonucleotide probe molecules of feature 1010 of microarray 1002. In actual cases, probe molecules may be much shorter relative to the length of the chromosome, and multiple, different, overlapping and non-overlapping probes/features may target a particular gene. Nonetheless, there is a definite, well-known correspondence between microarray features and genes.

The microarray may be exposed to sample solutions containing fragments of DNA. In one version of aCGH, an array may be exposed to fragments, labeled with a first chromophore, prepared from abnormal tissue and to fragments, labeled with a second chromophore, prepared from normal tissue. The normalized ratio of signal emitted from the first chromophore versus signal emitted from the second chromophore for each feature provides a measure of the relative abundance of the portion of the normal chromosome corresponding to the feature in the abnormal tissue versus the normal tissue. In the hypothetical microarray 1002 of FIG. 10, each feature corresponds to a different interval along the length of chromosome 407 and/408 in the hypothetical wild-type genome illustrated in FIG. 4. When fragments prepared from a normal tissue sample, labeled with a first chromophore, and DNA fragments prepared from normal tissue labeled with the second chromophore, are both hybridized to the hypothetical microarray shown in FIG. 10, and normalized intensity ratios for light emitted by the first and second chromophores are determined, the normalized ratios for all features should be relatively uniformly equal to one.

FIG. 11 represents an aCGH data set for two normal, differentially labeled samples hybridized to the hypothetical microarray shown in FIG. 10. The normalized ratios of signal intensities from the first and second chromophores are all approximately unity, shown in FIG. 11, by log ratios for all features of the hypothetical microarray 1002 displayed in the same color. By contrast, when DNA fragments isolated from tissues having the mutant genotype, illustrated in FIG. 5, labeled with a first chromophore are hybridized to the microarray, and DNA fragments prepared from normal tissue, labeled with a second chromophore, are hybridized to the microarray, then the ratios of signal intensities of the first chromophore versus the second chromophore vary significantly from unity in those features containing probe molecules equal to, or complementary to, subsequences of the amplified genes 430, 431, and 432. As shown in FIG. 12, increase in the ratio of signal intensities from the first and second chromophores, indicated by darkened features, are observed in those features 1202-1212 with probe molecules equal to, or complementary to, subsequences spanning the amplified genes 430, 431, and 432. Similarly, a decrease in signal intensity ratios indicates gene deletion in the abnormal tissues.

Microarray-based CGH data obtained from microarray experiments provide a relatively precise measure of the relative or absolute number of copies of genes in cells of a sample tissue. Sets of aCGH data obtained from pre-cancerous and cancerous tissues at different points in time can be used to monitor genome instability in particular pre-cancerous and cancerous tissues. Quantified genome instability can then be used to detect and follow the course of particular types of cancers. Moreover, quantified genome instabilities in different types of cancerous tissue can be compared in order to elucidate common chromosomal abnormalities, including gene amplifications and gene deletions, characteristic of different classes of cancers and pre-cancerous conditions. Unfortunately, biological data can be extremely noisy, with the noise obscuring underlying trends and patterns. Scientists, diagnosticians, and other professionals have therefore recognized a need for statistical methods for normalizing and analyzing aCGH data, in particular, and CGH data in general, in order to identify signals and patterns indicative of chromosomal abnormalities that may be obscured by noise arising from many different kinds of experimental and instrumental variations.

One approach to ameliorating the effects of high noise levels in CGH data involves, as a first step, normalizing sample-signal data by using control signal data. In many aCGH experiments, normal, control samples, including chromosomal DNA fragments of chromosomal DNA fragments, isolated from normal tissues are hybridized to arrays as control samples along with DNA fragments or copies isolated or produced from abnormal or diseased tissues for which a measure of chromosomal alterations or abnormalities is sought. Often, multiple control samples are available. Therefore, rather than simply using the log ratio of the signal generated by hybridization of fragments from diseased tissue to signal generated from one control sample, the signal generated from diseased tissue can be normalized using multiple control-sample-derived signals. It should be noted that the methods of the present invention may be applied to normalization of any signals produced from any type of sample, including diseased-tissue samples, samples produced by particular experiments, samples produced at particular times during particular experiments, and other samples of interest. The phrase "diseased tissue sample" is therefore interchangeable, in the following discussions, with the phrase "sample of interest."

As reviewed above, an aCGH array may contain a number of different features, each feature generally containing a particular type of probe, each probe targeting a particular chromosomal DNA subsequence indexed by index k that represents a genomic location. A subsequence indexed by index k is referred to as "subsequence k."

One can define the signal generated for subsequence k as the sum of the normalized log-ratio signals from the different probes targeting subsequence k divided by the number of probes targeting subsequence k or, in other words, the average log-ratio signal value generated from the probes targeting subsequence k, as follows:

$$C(k) = \frac{\sum_{b \in \{features\ containing\ probes\ for\ k\}} C(b)}{num\_features_k}$$

where $num\_features_k$ is the number of features that target the subsequence k;

C(b) is the normalized log-ratio signal measured for feature b, $$C(b) = \log\left(\frac{J_{red}}{J_{green}}\right)_b - \frac{\sum_{i \in \{all features\}} \log\left(\frac{J_{red}}{J_{green}}\right)_i}{num\_features}; \text{ and } \left(\frac{J_{red}}{J_{green}}\right)_i$$

signal $J_{green}$ for feature i.

In the case where a single probe targets a particular subsequence, k, no averaging is needed.

For convenience in description, C(k) is denoted from hereon as h.

As such, each aCGH data point may be viewed as a log ratio of signals read from a particular feature of a microarray that contains probes targeting a particular subsequence, the log-ratio of signals representing the ratio of signals emitted from a first label (e.g., red) used to label fragments of a genome sample and from a second label (e.g., green) used to label fragments of a normal, control genome. Both the sample-genome fragments and the normal, control fragments hybridize to normal-tissue-derived probe molecules on the microarray. A normal tissue or sample may be any tissue or sample selected as a control tissue or sample for a particular experiment. The term "normal" does not necessarily imply that the tissue or sample represents a population average, a non-diseased tissue, or any other subjective or object classification. The sample genome may be obtained from a diseased or cancerous tissue, in order to compare the genetic state of the diseased or cancerous tissue to a normal tissue, but may also be a normal tissue.

Subsequence deletions and amplifications generally span a number of contiguous subsequences of interest, such as genes, control regions, or other identified subsequences, along a chromosome. It therefore makes sense to analyze aCGH data in a chromosome-by-chromosome fashion, statistically considering groups of consecutive subsequences along the length of the chromosome in order to more reliably detect amplification and deletion.

Aspects of the invention include employing copy number aberration calling methods that account for a global noise component in the signal. Embodiments of the invention employ a combined noise factor (i.e., total noise factor) that includes both a local noise component (i.e., a probe-to-probe) noise component, and a global noise component. As such, it is assumed in embodiments of the invention that the noise of measurement includes both a local noise component that is independent for each subsequence along the chromosome, and independent for distinct probes (such that the local noise component is not correlated between different probes along the interval) and a global noise component, which noise component is correlated between probes along the interval.

Aspects of the invention include employing statistical measures to identify sets of consecutive subsequences for which deletion or amplification is relatively strongly indicated. This approach tends to ameliorate the effects of spurious, single-probe anomalies in the data. This approach is an example of an aberration-calling technique, in which gene-copy anomalies appearing to be above the data-noise level are identified.

As indicated above, where a total or combined noise component is employed, it is assumed that there are essentially two independent sources of noise contributing to the total noise intervals. These two sources are:
(1) a local noise component, $\sigma_{Local}$, which is not correlated between different probes along the interval, and;
(2) a global noise component, $\sigma_{Global}$, which is correlated between probes along the interval of interest.

$\sigma_{Local}^1$ is then employed to denote the local probe-to-probe noise.

As $\sigma_{Local}^1$ is not correlated between different probes, when k probes are averaged (using either mean or median), it is assumed that the local noise is reduced by a factor of $1/\sqrt{k}$. Thus, the measure of local noise that is employed in the determination of a combined noise factor is:

$$\sigma_{Local}^k = \sigma_{Local}^1/\sqrt{k}$$

Assuming that the local and global noise components are independent of each other, the combined noise, for an interval of length k, is described by the following equation:

$$\sigma^k = \sqrt{\sigma_{Local}^{k2} + (\sigma_{Global})^2}.$$

Substituting the term $\sigma_{Local}^k$, the following formula is obtained:

$$\sigma^k = \sqrt{\left(\frac{\sigma_{Local}^1}{\sqrt{k}}\right)^2 + (\sigma_{Global})^2} = \sqrt{\frac{{\sigma_{Local}^1}^2}{k} + (\sigma_{Global})^2}$$

Taking $\sigma_{Local}^1$ out of the square-root, and using $\alpha$ to denote $(\sigma_{Global}/\sigma_{Local}^1)^2$ the following equation is obtained as the measure of noise of an interval of length k:

$$\sigma^k = \sigma_{Local}^1 \sqrt{\frac{1}{k} + \alpha}$$

As can be seen from the above, the above measure of noise includes a combined noise factor that accounts for both local noise and global noise.

Where desired, the above combined noise factor may be employed in a statistical scoring based protocol of identifying chromosomal aberrations as follows.

One can consider the measured, normalized, or otherwise processed signals for subsequences along the chromosome of interest to be a vector V as follows:

$$V = \{v_1, v_2, \ldots, v_n\}$$

where $v_k = C(k)$ where $v_k = h$, as defined above.

Note that the vector, or set V, is sequentially ordered by position of subsequences along the chromosome. As such, in the first step of embodiments of the invention, one obtains a vector of signals comprising normalized hybridization levels for fragments of a biopolymer sequence, e.g., chromosome. Next, a set of intervals is generated within the vector of signals. As mentioned below, the interval length may be varied as desired.

A statistic S is computed for each interval I of subsequences along the chromosome as follows:

$$\text{Score}(I) = \frac{h}{\sigma^k}$$

Since the combined noise component can be rewritten as:

$$\sigma^k = \sigma_{Local}^1 \sqrt{\frac{1}{k} + \alpha}$$

The following equation can also be employed to obtain a statistical score:

$$\text{Score}(I) = \frac{h}{\sigma_{Local}^1 \sqrt{\frac{1}{k} + \alpha}}$$

where:
where $I = v_i, \ldots, v_j$
with each interval containing k probes, and h is the average log ratio signal of the k probes over the given interval.

In this way, each interval is scored with a statistical score, where the statistical score is determined using a combined noise factor that includes a local and global noise factor Under a null model assuming no sequence aberrations, the statistic S has a normal distribution of values with mean=0 and variance=1, independent of the number of probes included in the interval I. The statistical significance of the normalized signals for the subsequences in an interval I can be computed by a standard probability calculation based on the area under the normal distribution curve:

$$\text{Prob}(|S(I)| > z) \approx \left(\frac{1}{\sqrt{2\pi}}\right)\frac{1}{z}e^{-\frac{z^2}{2}}$$

Alternatively, the magnitude of S(I) can be used as a basis for determining alteration.

It should be noted that various different interval lengths may be used, iteratively, to compute amplification and deletion probabilities over a particular biopolymer sequence. In other words, a range of interval sizes can be used to refine amplification and deletion indications over the biopolymer.

Figure 13:
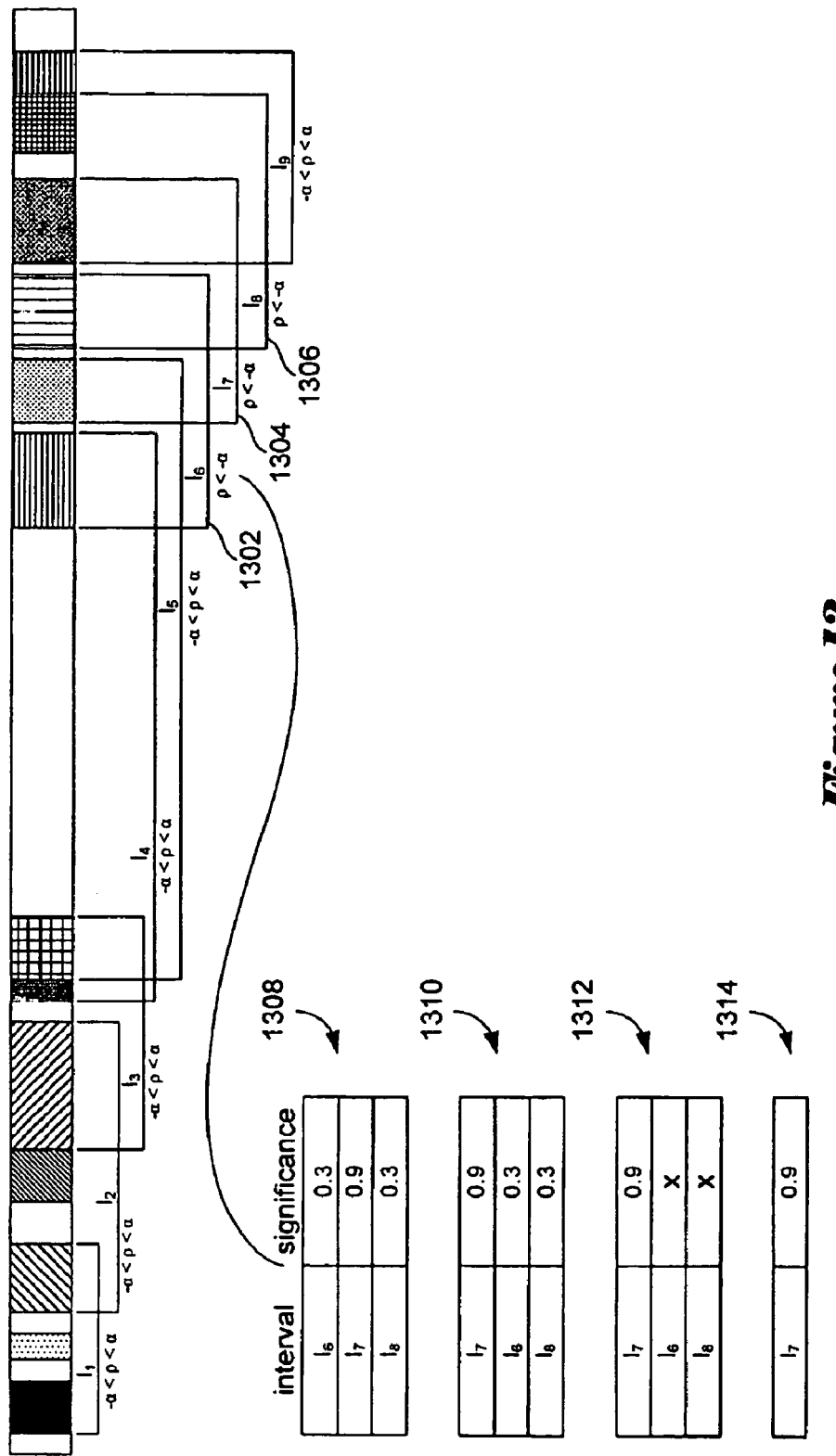
FIG. 13 illustrates one method for identifying and ranking intervals and removing redundancies from lists of intervals identified as probable deletions or amplifications.

After the probabilities for the observed values for intervals are computed, those intervals with computed probabilities outside of a reasonable range of expected probabilities under the null hypothesis of no amplification or deletion are identified, and redundancies in the list of identified intervals are removed. In this way, intervals with statistical scores that differ from a threshold range bounded by a first threshold value and a second threshold value are identified as comprising copy number aberrations, e.g., deletions or amplifications, in the biopolymer sequence, e.g., chromosome. FIG. 13 illustrates one method for identifying and ranking intervals and removing redundancies from lists of intervals identified as corresponding to probable deletions or amplifications. In FIG. 13, the intervals for which probabilities are computed along the chromosome $C_1$ (402 in FIG. 4) for diseased tissue with an abnormal chromosome (502 in FIG. 5) are shown. Each interval is labeled by an interval number, $I_x$, where x ranges from 1 to 9. For most intervals, the calculated probability falls within a range of probabilities consonant with the null hypothesis. In other words, neither amplification nor deletion is indicated for most of the intervals. However, for intervals $I_6$ 1302, $I_7$ 1304, and $I_8$ 1306, the computed probabilities fall below the range of probabilities expected for the null hypothesis, indicating potential subsequence deletion in the diseased-tissue sample. (Note that if the computed probabilities were above the range of probabilities expected for the null hypothesis, potential subsequence amplification in the diseased-tissue sample would be indicated. These three intervals are placed into an initial list 1308 which is ordered by the significance of the computed probability into an ordered list 1310. Note that interval $I_7$ 1304 exactly includes those subsequences deleted in the diseased-tissue chromosome (502 in FIG. 5), and therefore reasonably has the highest significance with respect to falling outside the probability range of the null hypothesis. Next, all intervals overlapping an interval occurring higher in the ordered list are removed, as shown in list 1312, where overlapping intervals $I_6$ and $I_8$, with less significance, are removed, as indicated by the character X placed into the significance column for the entries corresponding to intervals $I_6$ and $I_8$. The end result is a list containing a single interval 1314 that indicates the interval most likely coinciding with the deletion. The final list for real chromosomes, containing thousands of subsequences and analyzed using hundreds of intervals, may generally contain more than a single entry. Additional details regarding computation of interval scores can be found in "Efficient Calculation of Interval Scores for DNA Copy Number Data Analysis," Lipson et al., Proceedings of RECOMB 2005, LNCS 3500, p. 83, Springer-Verlag.

In certain embodiments where a combined noise factor is employed, it may be desirable to determine, e.g., in the form of an estimated value, the local probe-to-probe noise $\sigma_{Local}^1$ and $\alpha$. $\sigma_{Local}^1$ may be estimated using derivative log ratio spread (dlrs):

$$\sigma_{Local}^1 = dlrs(v) = \frac{IQR(\partial v)}{\sqrt{2} \times 1.349}$$

In order to estimate $\alpha$, the combined noise $\sigma^k$ is first estimated, e.g., by binning consecutive probes into bins of size $k=\sqrt{n}$. A binned vector u is derived by averaging each bin (using either mean or median) into a single number. $\sigma^k$ is estimated by dlrs(u). To make this estimation more robust, binning may be repeated using different "frame-shifts" of the first bin. The final estimation of $\sigma^k$ is the median of the different estimation.

Finally, $\alpha$ is estimated using the estimated $\sigma^k$ and $\sigma_{Local}^1$ values in the formula:

$$\sigma^k = \sigma_{Local}^1 \sqrt{\frac{1}{k} + \alpha}$$

and solving for $\alpha$.

The user may employ these estimated values of $\sigma_{Local}^1$ and $\alpha$ as desired.

In addition to the above, $\alpha$ may be estimated using alternative methods. Certain of these methods employ signal/noise estimation.

Given a log-ratio vector v of length n, and a significance threshold level tau, an alternative way to estimate $\alpha$ may employ the following iterative process:

Starting with an initial estimation of alpha (0.01), repeat the following steps: a) Calculate the list of all aberrant regions that have a score (equation (2) above), above tau. Note that this score depends on the current value of $\alpha$. This list of aberrations may be regarded as the "Signal" component of the data; b) Compute the residual vector r—subtract the called aberrations from the vector v. The vector r represent our current estimation of the noise; and c) Estimate $\sigma^k$ from the residual vector r, as explained in the previous subsection, and the resulting new $\alpha$, until the process converges (new alpha is very close to alpha).

In certain embodiments, a score based on global error may applied only to intervals with height larger than user defined constant.

In other embodiments, $\sigma^k = \min_{1 \leq k \leq K} \sigma^k$, for some K that depends on the number of probes on the array, e.g. $K=\sqrt{N}$, where N is the total number of probes on the array.

$\sigma^k$ may be bounded by some user defined constant in certain embodiments.

Aspects of the invention may score all intervals using a scoring protocol that employs a combined noise factor which includes a global noise component, as described above. Alternatively, the combined noise scoring factor may only be employed in aberration calling when an interval provides a signal having a height that is less than a predetermined threshold or constant, e.g., less than about 0.5, such as less than about 0.3, including less than about 0. In these embodiments, a dual type scoring protocol may be employed, where a combined noise scoring protocol such as that described above is employed for the intervals having signals with heights less than the predetermined threshold and a local noise only scoring protocol is employed for those intervals having a height above the predetermined threshold. Local noise based scoring protocols of interest include those described in application Ser. Nos. 10/953,958; 11/338,515; and 11,363,699; the disclosures of which scoring protocols are herein incorporated by reference. Alternatively or in addition, intervals having a number of probes that falls within a predetermined range may be scored with a predetermined minimum combined noise factor. For example, one may define the minimum combined noise factor range as ranging from 1 to the square root of the total number of probes on an array (K). Using this range, if the total number of probes of an interval k falls in the range of 1 to K, then the minimum combined noise factor is employed in scoring that interval. Alternatively or in addition, one may bound the total combined noise factor by an upper and/or lower predetermined limit. In such situations, if the empirically determined combined noise factor falls above the upper limit of the predetermined bounded range, the upper limit is employed. Likewise, if the empirically determined combined noise factor falls below the lower limit of the predetermined bounded range, the lower limit is employed.

Various embodiments of the present invention may employ a centralization constant, e.g., as described in U.S. application Ser. No. 11/338,515; the disclosure of which centralization constant based methods is herein incorporated by reference. Briefly, in such methods one may determine a zero point, or centralization constant $\zeta$, for an array-based comparative genomic hybridization ("aCGH") data set by identifying a zero-point value, or centralization constant $\zeta$, that, when used in an aberration-calling analysis of the aCGH data, results in the fewest number of array-probe-complementary genomic sequences identified as having abnormal copy numbers with respect to a control genome, or, in other words, results in the greatest number of array-probe-complementary genomic sequences identified as having normal copy numbers. In one embodiment, interval-based analysis of an aCGH data set may be carried out using a range of putative zero-point values, and the zero-point value for which the maximum number of genomic sequences are determined to have normal copy numbers may then be selected.

The subject method includes executing computer-readable instructions that are at a remote location to the user, and transmitting data from the remote location to the graphical user interface at the user's location. In certain embodiments, the data sets may be received from a remote location, and the programming executed locally to the user.

The above-described computer-implemented method may be executed using programming that may be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

Appropriate operating systems for use in conjunction with the programming include, but are not limited to, Solaris (Sun Microsystems, Inc., Santa Clara, Calif.), Windows (Microsoft Corp., Redmond, Wash.), Mac (Apple Computer, Inc., Cupertino, Calif.), or Linux (Red Hat, Inc., Raleigh, N.C.). Appropriate software applications include, but are not limited to, relational databases such as Oracle 9.0.1 (9i) (Oracle Corp., Redwood Shores, Calif.), DB2 Universal Database V8.1 (IBM Corp., Armonk, N.Y.), PostgreSQL (PostgreSQL, Inc., Wolfville, NS Canada), or SQL Server 2000 (Microsoft Corp., Redmond, Wash.).

As noted above, one embodiment involves two tiers of infrastructure: a server tier and a client tier. In one embodiment, the server tier may be an workgroup server (Sun Microsystems, Inc., Santa Clara, Calif.), the operating system may be Solaris (Sun Microsystems, Inc., Santa Clara, Calif.), and the database software may be Oracle 9.0.1 (9i) (Oracle Corp., Redwood Shores, Calif.). In the same embodiment, the client tier may operate using the Windows operating system (Microsoft Corp., Redmond, Wash.). In this embodiment, a Java language-based application, running on the client may contain both business and presentation logic. A Java Runtime Engine (JRE) may interpret and execute the compiled application within the client operating system (e.g. Windows). In addition to proprietary presentation and business logic, the client application may rely on third party application programming interfaces (APIs) for common functionality such as application connectivity and database connectivity. Installing APIs and a database on a server may provide a scalable solution for information sharing and propagating updates among numerous client applications. Each client may communicate with a server-based APIs through the local area network using common protocols (e.g. TCP/IP) supported by both the client and server operating systems (e.g. Windows and Solaris).

Computer Readable Media

In certain embodiments, the above-described methods are coded onto a computer-readable medium in the form of programming, where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

In certain embodiments, a computer-readable medium comprising instructions for producing the above-described graphical user interface is provided.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A computer-based system comprising the above-referenced computer readable medium is also provided. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

One or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Sun Solaris, Linux, OS/400, Compaq Tru64 Unix, SGI IRIX, Siemens Reliant Unix, and others.

In certain embodiments, the subject devices include multiple computer platforms which may provide for certain benefits, e.g., lower costs of deployment, database switching, or changes to enterprise applications, and/or more effective firewalls. Other configurations, however, are possible. For example, as is well known to those of ordinary skill in the relevant art, so-called two-tier or N-tier architectures are possible rather than the three-tier server-side component architecture represented by, for example, E. Roman, Mastering Enterprise JavaBeans™ and the Java™ 2 Platform (John Wiley & Sons, Inc., NY, 1999) and J. Schneider and R. Arora, Using Enterprise Java. (Que Corporation, Indianapolis, 1997).

It will be understood that many hardware and associated software or firmware components that may be implemented in a server-side architecture for Internet commerce are known and need not be reviewed in detail here. Components to implement one or more firewalls to protect data and applications, uninterruptable power supplies, LAN switches, web-server routing software, and many other components are not shown. Similarly, a variety of computer components customarily included in server-class computing platforms, as well as other types of computers, will be understood to be included but are not shown. These components include, for example, processors, memory units, input/output devices, buses, and other components noted above with respect to a user computer. Those of ordinary skill in the art will readily appreciate how these and other conventional components may be implemented.

The functional elements of system may also be implemented in accordance with a variety of software facilitators and platforms (although it is not precluded that some or all of the functions of system may also be implemented in hardware or firmware). Among the various commercial products available for implementing e-commerce web portals are BEA WebLogic from BEA Systems, which is a so-called "middleware" application. This and other middleware applications are sometimes referred to as "application servers," but are not to be confused with application server hardware elements. The function of these middleware applications generally is to assist other software components (such as software for performing various functional elements) to share resources and coordinate activities.

Other development products, such as the Java™ 2 platform from Sun Microsystems, Inc. may be employed in the system to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

Additional system components, methods, arrays and kits may be include as are described in U.S. patent application Ser. No. 11/001700, filed Nov. 30, 2004, U.S. patent application Ser. No. 11/001672, filed Nov. 30, 2004 and U.S. patent application Ser. No. 11/000681, filed Nov. 30, 2004, the entireties of which are incorporated by reference herein.

Kits

Kits for use in connection with the subject invention may also be provided. Such kits may include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading array analysis software. Alternately, the combination may be provided in connection with new software. In certain embodiments, the instructions will serve as a reference manual (or a part thereof) and the computer readable medium as a backup copy to the preloaded utility.

The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

Utility

The nuclear genome of the cells of a plurality of cellular samples may be evaluated using the above-described method. In one embodiment, the method may be employed to identify deletions, insertions, and other chromosomal aberrations, that are common to many different samples.

Arrays employed in CGH assays contain polynucleotides immobilized on a solid support. Array platforms for performing the array-based methods are generally well known in the art (e.g., see Pinkel et al., Nat. Genet. (1998) 20:207-211; Hodgson et al., Nat. Genet. (2001) 29:459-464; Wilhelm et al., Cancer Res. (2002) 62: 957-960) and, as such, need not be described herein in any great detail. In general, CGH arrays contain a plurality (i.e., at least about 100, at least about 500, at least about 1000, at least about 2000, at least about 5000, at least about 10,000, at least about 20,000, usually up to about 100,000 or more) of addressable features that are linked to a planar solid support. Features on a subject array usually contain a polynucleotide that hybridizes with, i.e., binds to, genomic sequences from a cell. Accordingly, such "comparative genome hybridization arrays", for short "CGH arrays" typically have a plurality of different BACs, cDNAs, oligonucleotides, or inserts from phage or plasmids, etc., that are addressably arrayed. As such, CGH arrays usually contain surface bound polynucleotides that are about 10-200 bases in length, about 201-5000 bases in length, about 5001-50,000 bases in length, or about 50,001-200,000 bases in length, depending on the platform used.

In particular embodiments, CGH arrays containing surface-bound oligonucleotides, i.e., oligonucleotides of 10 to 100 nucleotides and up to 200 nucleotides in length, find particular use in the subject methods.

In general, the subject assays involve labeling a test and a reference genomic sample to make two labeled populations of nucleic acids which may be distinguishably labeled, contacting the labeled populations of nucleic acids with an array of surface bound polynucleotides under specific hybridization conditions, and analyzing any data obtained from hybridization of the nucleic acids to the surface bound polynucleotides. Such methods are generally well known in the art (see, e.g., Pinkel et al., Nat. Genet. (1998) 20:207-211; Hodgson et al., Nat. Genet. (2001) 29:459-464; Wilhelm et al., Cancer Res. (2002) 62: 957-960)) and, as such, need not be described herein in any great detail.

Two different genomic samples may be differentially labeled, where the different genomic samples may include an "experimental" sample, i.e., a sample of interest, and a "control" sample to which the experimental sample may be compared. In certain embodiments, the different samples are pairs of cell types or fractions thereof, one cell type being a cell type of interest, e.g., an abnormal cell, and the other a control, e.g., a normal cell. If two fractions of cells are compared, the fractions are usually the same fraction from each of the two cells. In certain embodiments, however, two fractions of the same cell type may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells, or in different phases of the cell cycle) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Results obtained from several of such array-based CGH assays may be analyzed using the methods described above to identify common aberrations.

The following examples are offered by way of illustration and not by way of limitation.

Experimental

Array comparative genomic hybridization (aCGH) data are obtained for two samples, i.e., an 18q dilution series sample and HT29 sample, using the Agilent Human Genome CGH Microarray 44A aCGH system (Agilent Technologies, Santa Clara, Calif.) according to the manufacturer's instructions. Two different scoring protocols for the data are employed. The first scoring protocol is a local noise only scoring protocol employed in an aberration calling protocol identified as ADM-1, as disclosed in application Ser. Nos. 10/953,958; 11/338,515; and 11/363,699. This scoring protocol is described as follows:

$$S(I) = \left( \sum_{k=i,\dots,j} v_k \right) \cdot \frac{1}{\sqrt{j-i+1}} \text{ or } S(I) = \frac{h}{\sqrt{k}}$$

The second aberration calling protocol that was employed with the data was the ADM-1 aberration calling protocol that employed the combined noise scoring protocol described as follows:

$$\text{Score}(I) = \frac{h}{\sigma^k}$$

Figure 14A:
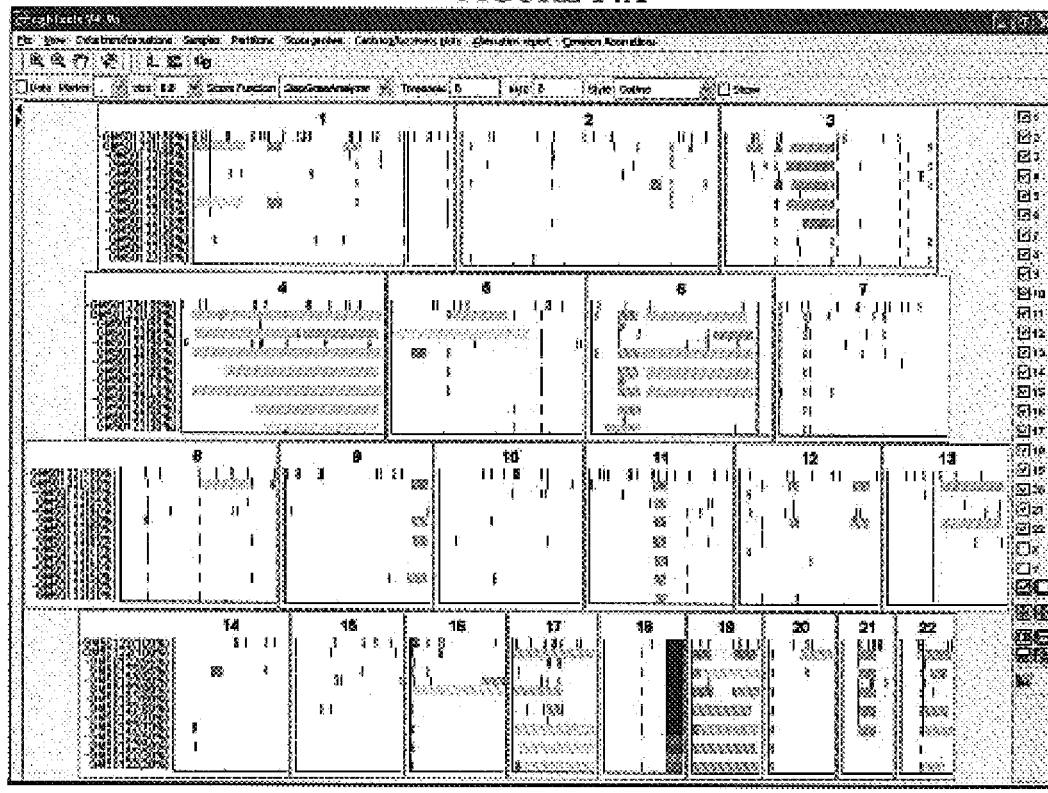
FIGS. 14A-16 show screen captures that comparative visual results of a CGH aberration calling protocol applied to the same aCGH data using either a local noise only based scoring protocol or a combined noise scoring protocol in accordance with the present invention.
Figure 14B:
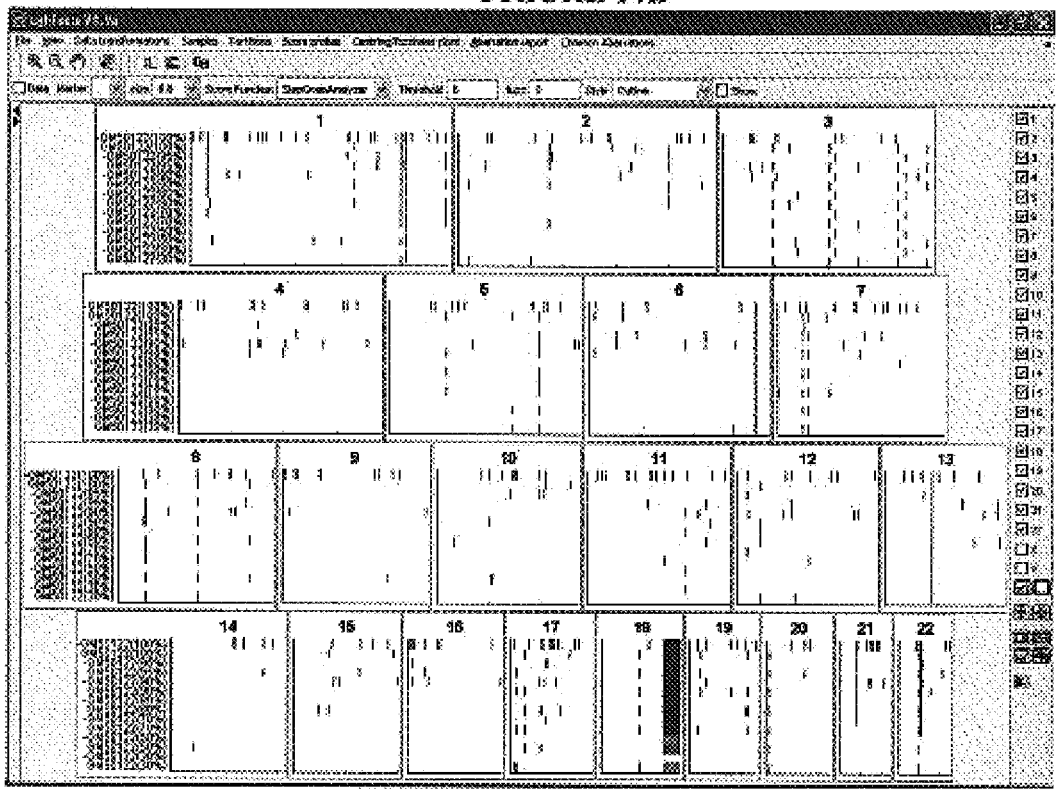

FIG. 14A provides a screen capture of a graphical user interface which provides results from using the ADM-1 aberration calling protocol on data obtained from an 18q dilution series. FIG. 14B provides a graphical user interface of the same data when the combined noise scoring protocol of the present invention is employed. As can be seen in comparing the results, low height (shown as light green and light red) aberrations shown in FIG. 14A, are not called significant using the combined noise protocol (i.e.global error model).

Figure 15A:
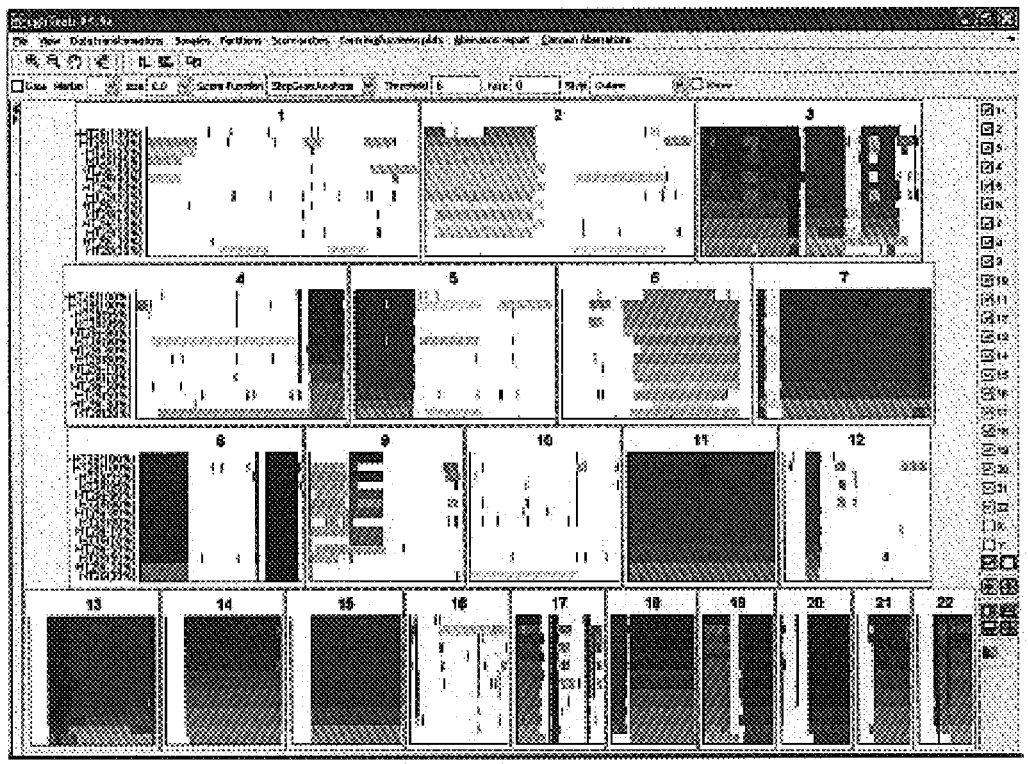
Figure 15B:
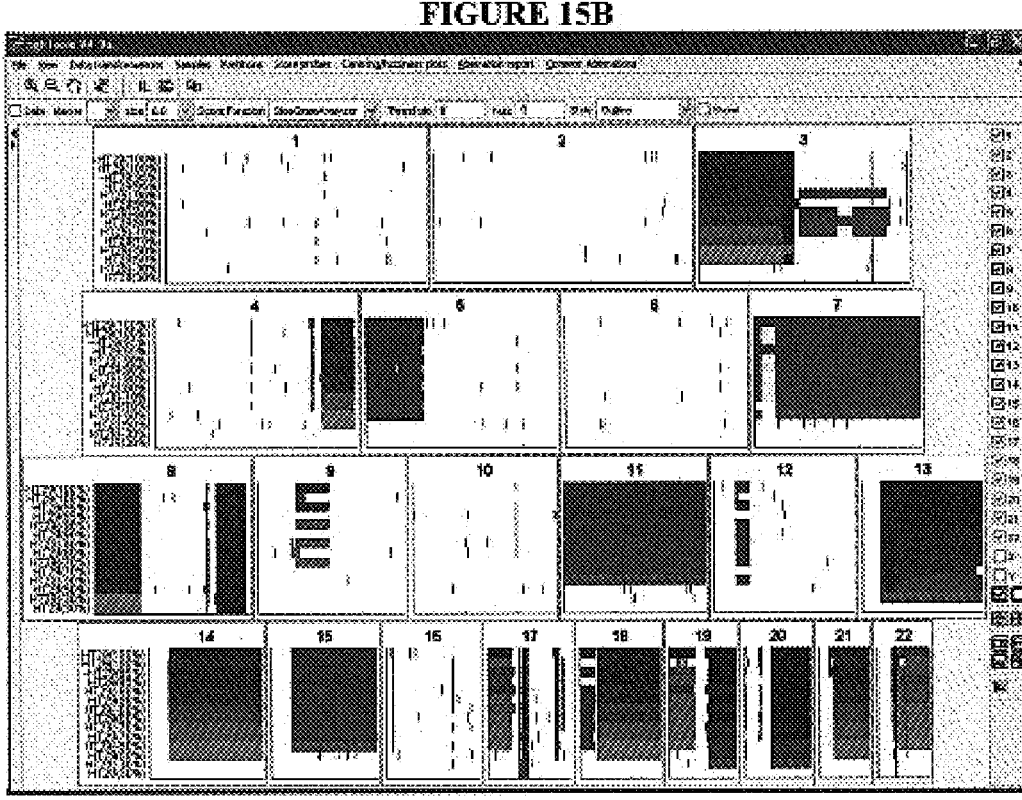

FIG. 15A provides a screen capture of a graphical user interface which provides results from using the ADM-1 aberration calling protocol on data obtained from an HT29 sample. FIG. 15B provides a graphical user interface of the same data when the combined noise scoring protocol of the present invention is employed aberrations of height less than 0.3. As can be seen in comparing the results, low height (shown as light green and light red) aberrations shown in FIG. 15A, are not called significant using the combined noise protocol (i.e.global error model).

Figure 16:
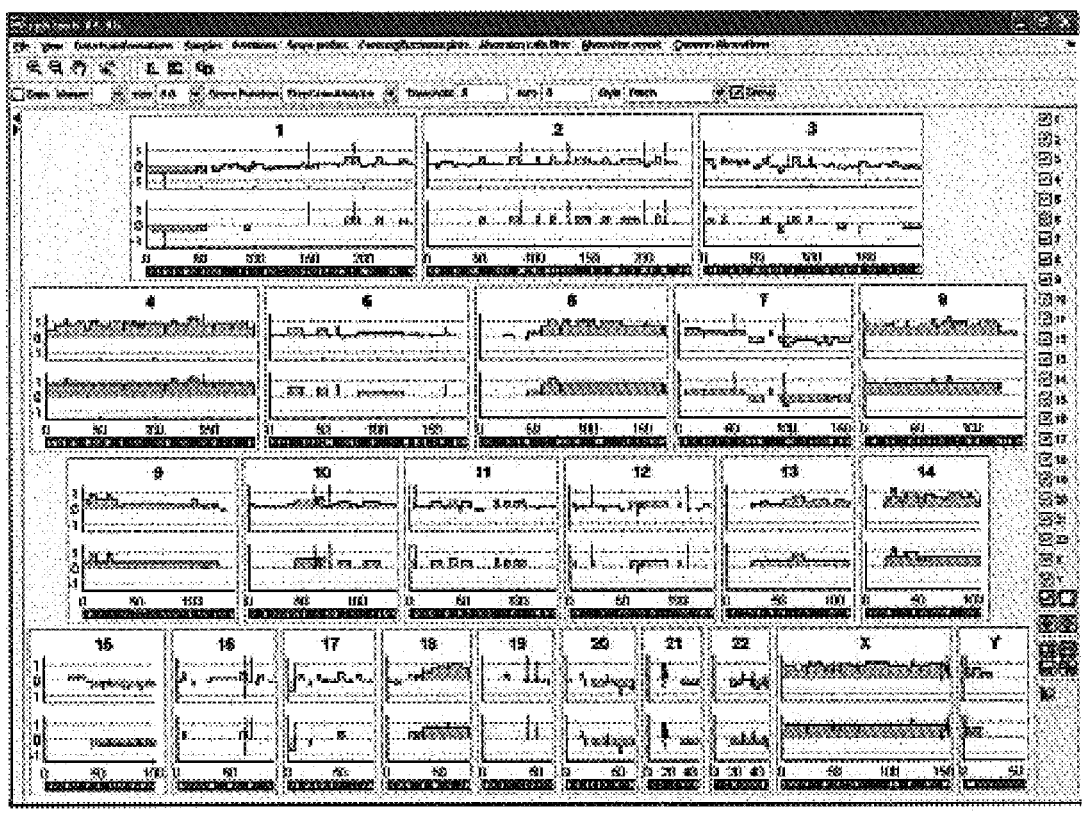

Finally, FIG. 16 provides a screen capture of a graphical user interface providing a comparison of aberration calls for ADM-1, and AMD-1 with global error model applied to aberrations of height less than 0.

These results demonstrate that the use of an aberration calling protocol that employs a scoring protocol based on a combined noise factor which includes a global noise component can effectively improve the results that are obtained.

Although the present invention has been described in terms of a particular embodiment, it is not intended that the invention be limited to this embodiment. Modifications within the spirit of the invention will be apparent to those skilled in the art. For example, an almost limitless number of different implementations of computer programs and computer-program routines can be created to compute the above-described analysis methods for analyzing chromosomal aberrations in diseased-tissue samples when a number of control samples are available. Although recursive methods may be employed, more efficient, non-recursive algorithms can be employed to more efficiently compute the desired statistics. The above-described methods can be easily modified to encompass experimental data from many different organisms having different numbers of chromosomes, different numbers of subsequences per chromosome, and other genetic differences. In each component of the above-described method, many possible mathematically similar, but alternative approaches may be employed. For example, different methods for computing means and variances can be used, as well as different statistical parameters used to characterize particular distributions.

Many different types of user-interface implementations, in addition to the user-interface implementation discussed above with reference to FIGS. 14A-16F can be employed to allow for convenient selection of parameters that control CGH analysis and various different CGH-data-analysis-results display formats.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A method for identifying copy number aberrations in a biopolymer sequence of a sample, said method comprising:

obtaining a vector of signals comprising normalized hybridization levels for fragments of said biopolymer sequence;

generating a set of intervals within the vector of signals;

scoring each interval with a statistical score, wherein said statistical score is determined by a computer using a combined noise factor that includes a local and global noise factor; and determining intervals with statistical scores that below a first threshold as likely deleted and intervals with statistical scores above a second threshold as likely amplified.

2. The method according to claim 1, wherein said local noise component is a measure of probe-to-probe noise that is not correlated between different probes along an interval.

3. The method according to claim 1, wherein said global noise component is a measure of noise that is correlated between different probes along an interval.

4. The method according to claim 1, wherein said method further comprises determining said normalized hybridization levels for fragments of the biopolymer sequence.

5. The method according to claim 4, wherein said normalized hybridization levels are determined using hybridization levels for fragments of biopolymer sequences obtained from one or more control samples, with respect to each of a set of consecutive subsequences of a standard biopolymer sequence.

6. The method of claim 1 wherein determining intervals with statistical scores that differ from a threshold range further includes comparing a probability of observing the statistical score for each interval with the first and second thresholds.

7. The method of claim 1 wherein the biopolymer sequence is a DNA sequence.

8. The method of claim 1 wherein hybridization levels for fragments of the biopolymer sequence are determined by an array-based, comparative hybridization method.

9. The method of claim 1 wherein a predetermined total combined noise factor is employed in said scoring when the number of probes per interval falls within a predetermined range.

10. The method of claim 1 wherein said total combined noise factor has a value falling within a user defined predetermined range.

11. The method of claim 1 wherein when a given interval has a signal level that exceeds a predetermined value, an alternative scoring protocol is employed for that interval.

12. The method of claim 11 wherein said alternative scoring protocol scores said interval based on a local noise factor.

13. The method of claim 1, wherein said method includes estimating a using an iterative process.

14. The method of claim 13, wherein said iterative process employs a signal to noise estimate.

15. A computer readable storage medium comprising a computer executable program that implements the method of claim 1 on a computer.

* * * * *

UNITED STATES PATENT AND TRADEMARK OFFICE
CERTIFICATE OF CORRECTION

PATENT NO. : 7,660,675 B2
APPLICATION NO. : 11/492472
DATED : February 9, 2010
INVENTOR(S) : Jayati Ghosh et al.

It is certified that error appears in the above-identified patent and that said Letters Patent is hereby corrected as shown below:

In column 22, line 24, in claim 13, delete "a" and insert -- α --, therefor.

Signed and Sealed this

Twenty-fifth Day of May, 2010

David J. Kappos
*Director of the United States Patent and Trademark Office*